US00PP11641P

United States Patent [19]

Olesen et al.

[11] Patent Number: Plant 11,641

[45] Date of Patent: Nov. 21, 2000

[54] COMPACT FLORIBUNDA ROSE PLANT NAMED 'POULPEAR'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/138,035

[22] Filed: Aug. 18, 1998

[51] Int. Cl.[7] ..... A01H 5/00

[52] U.S. Cl. ..... Plt./146

[58] Field of Search ..... Plt./146, 141, 143

[56] References Cited

U.S. PATENT DOCUMENTS

P.P. 5,770 7/1986 de Ruiter ..... Plt./122

*Primary Examiner*—Howard J. Locker

[57] ABSTRACT

A new floribunda rose plant which has abundant pale orange colored flowers, compact and vigorous growth, and abundant dark green foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of compact floribunda rose plant which originated from a controlled crossing between an unnamed seedling and 'RUImired', U.S. Plant Pat. No. 5,770. The two parents were crossed and the resulting seeds were planted in a controlled environment. The new variety is named 'POULpear'.

The new rose may be distinguished from its seed parent, an unnamed seedling created by the same inventors, by the following combination of characteristics:

1. 'POULpear' is a compact floribunda with pale orange colored flowers and the unnamed seedling is a grandiflora with bright orange flowers.

2. The unnamed seedling resulted from a crossing of 'POULetta' and 'Amber Queen'.

The new variety may be distinguished from its pollen parent, 'RUImired', by the following combination of characteristics:

1. 'POULpear' is a compact floribunda with pale orange colored flowers whereas 'RUImired' is miniature rose with orange-red flowers.

2. The foliage and flowers of 'POULpear' are larger than 'RUImired'.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULpear' was selected by the inventors as a single plant from the progeny of the hybridization in April, 1993.

Asexual reproduction of 'POULpear' by cuttings and traditional budding was first done by L. Pernille and Mogens N. Olesen in their nursery in Fredensborg, Denmark in July, 1993. This initial and other subsequent propagations conducted in controlled environments have demonstrated that the characteristics of 'POULpear' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULpear' from a field nursery. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns; and

6. Leaves.

DETAILED DESCRIPTION OF THE VARIETY

The following is a description of 'POULpear', as observed in its growth in glasshouses in Fredensborg, Denmark, Half Moon Bay, Calif. and in field nursery in Applegate, Jackson County, Oreg. Color references are made using The Royal Horticultural Society (London, England) Colour Chart, 1995, except where common terms of color are used.

For a comparison, the nearest existing rose variety is 'POULrek' a patented variety by the same inventors described and illustrated in U.S. Plant Pat. No. 9,688 and issued on Nov. 12, 1996. Chart 1 details several physical characteristics of 'POULpear' and 'POULrek'.

CHART 1

| | 'POULpear' | 'POULrek' |
|---|---|---|
| Upper petal surface, open bloom | Orange Group 27A on outermost petals and blend of Orange Group 27A and Yellow-Orange Group 19A on innermost petals | Red Group 36D |

-continued

CHART 1

| | 'POULpear' | 'POULrek' |
|---|---|---|
| Color, upper petal surface, after opening | Orange Group 27A on outermost petals and blend of Orange Group 27A and Yellow-Orange Group 19A on innermost petals | Red Group 36D |
| Color, basal petal spot. | Yellow Group 5B-5C. | Yellow Group 4D |

Parents: Unnamed seedling×'RUImired'.
Classification:
*Botanical.*—Rosa hybrida.
*Commercial.*—Compact floribunda.

FLOWER AND FLOWER BUD

Blooming habit: Recurrent.
Flower bud:
*Size.*—Upon opening, 20 mm–25 mm in length from base of receptacle to flower tip.
*Bud form.*—Ovoid to globular.
*Bud color.*—A blend of Orange Group 27A and 24C at ¼ opening.
*Sepals.*—Green Group 143B. On plants grown under high light conditions, sepals exhibit intonations of Greyed-Red Group 184A. Weak to moderate foliaceous appendages on three of the five sepals. Exterior surfaces of the sepals moderately pubescent. Stipitate glands present on margins of sepals with appendages.
*Peduncle.*—Surface: Limited to moderate numbers of fine hairs and stipitate glands. Length: 15 mm to 40 mm range of length. Color: Green Group 143C. On plants grown under high light conditions, peduncles exhibit intonations of Greyed-Red Group 184A–B. Strength: Upright.
*Receptacle.*—Surface: With a moderate number of fine hairs. Shape: Broadly urn-shaped. Size: Medium. 6 mm (height)×8 mm (width) on average. Color: Green Group 143C to 143D.
*Borne.*—Generally with one to three buds per flowering stem.
Flower bloom:
*Size.*—Medium to large for a 15 cm–17 cm pot rose. Average diameter is 60 mm–65 mm when open.
*Form.*—Petals reflex. Shape of flower when viewed from the side: Upon opening, upper part: Convex. Upon opening, lower part: Flat. Open flower, upper part: Flattened convex. Open flower, lower part: Flat.
*Petalage.*—Double to very double. Average range: 30–40 under normal conditions with 10–15 petaloids.
Color:
*Upon opening.*—Outermost petals: Upper Surface: Blend of Orange Group 27A and Yellow-Orange 19B. Reverse Surface: Orange Group 27A. Innermost petals: Upper Surface: Blend of Orange Group 27A and Yellow-Orange 19A. Reverse Surface: Orange Group 27A.
*After opening.*—Outermost petals: Upper Surface: Orange Group 27A. Reverse Surface: Orange Group 27A. Innermost petals: Upper Surface: Blend of Orange Group 27A and Yellow-Orange Group 19A. Reverse Surface: Orange Group 27A.
Basal petal spots: A spot exists on the outer side and inner side of the base of the petal.
*Upon opening.*—Outermost petals: Outer Side: Green-White Group 157B. Inner Side: Yellow Group 5B. Innermost petals: Outer Side: Green-White Group 157B. Inner Side: Yellow Group 5B.
*After opening.*—Outermost petals: Outer Side: Green-White 157B. Inner Side: Yellow Group 5C. Innermost petals: Outer Side: Green-White Group 157B. Inner Side: Yellow Group 5C.
General tonality: No change in the general tonality at the end of the first day. Afterwards, general tonality gradually changes to Orange Group 27B.
Petals:
*Petal reflex.*—Petals reflex backwards slightly.
*Petaloids.*—Present. Quantity: 10–15.
*Fragrance.*—Light, fresh fragrance.
*Duration.*—As a pot plant, flowers last from 6 to 8 days. As a cut flower 5 to 6 days.
*Texture.*—Moderate.
*Shape.*—Round. Inner petals narrower.
*Form.*—Inner petals reflexed slightly. Outermost petals double reflexed.
*Arrangement.*—Regular.
Reproductive organs:
*Pollen.*—Color: Yellow-Orange Group 22A. Abundance: Average.
*Anthers.*—Size: Medium. Color: Yellow-Orange Group 22A.
*Filaments.*—Color: Yellow-Green Group 150C.
*Stigmas.*—At or slightly superior in location to anthers. Color: Green-White Group 157C with intonations of Greyed-Red Group 179A.
*Styles.*—Color: Green-White Group 157C.
*Hips.*—None observed.

PLANT

Plant growth: Vigorous, compact, upright to bushy. When grown as a 15 cm pot plant, the average height of the plant itself is 22 to 25 cm and the average width is 22 cm. When grown as a nursery plant on its own roots, the average plant height is 60–75 cm and the average width is 60–75 cm.
Stems:
*Color.*—Young wood: Green Group 137C. On plants grown under high light conditions, young wood exhibits intonations of Greyed-Red Group 184B. Older wood: Green Group 137B.
*Thorns.*—Incidence: Moderate thorns. Size: Average length: 6 mm–7 mm. Color: Younger wood: Red Group 38D. Older wood: Greyed-Orange Group 177A. Shape: Linear to slightly curved downward.
*Bark.*—Young wood: Smooth. Older wood: Smooth.
Plant foliage: Normal number of leaflets on normal leaves in middle of the stem: 5 leaflets. Some leaves with 7 leaflets.
*Leaf size.*—Medium to large. 90 mm (l)×65 mm (w).
*Abundance.*—Abundant.
*Color.*—Upper Leaf Surface: Green Group 137A–139A. Lower Leaf Surface: Green Group 138B. On plants grown under high light conditions, lower leaf surfaces may exhibit intonations of Greyed-Red Group 180B. Juvenile foliage: Upper leaf surface: Green Group 137A. On plants grown under high light conditions; upper leaf surfaces, petioles and rachis exhibit intonations of Greyed- Red Group 180B. Lower leaf surface: Green Group 137A. On plants grown under high light conditions; lower leaf surfaces, petioles and rachis exhibit intonations of Greyed-Red Group 180B.

Plant leaves and leaflets:

*Stipules*.—Present. Size: 10 mm–12 mm. Color: Green Group 138B. Presence of hairs: On margins.

*Petiole*.—Length: 15 mm–25 mm. Color: Green Group 137B. Underneath: With limited number of hairs and prickles.

*Rachis*.—With limited number of small prickles underneath. Color: Green Group 137B.

*Leaflet edge*.—Serrated.

*Shape*.—Leaflets are: Ovate.

*Leaflets*.—Number: Generally 5.

*Other*.—Moderately glossy. Thick texture.

Disease resistance: Above average resistance to mildew, black spot and Botrytis under normal growing conditions in Half Moon Bay, Calif. and Fredensborg, Denmark.

We claim:

1. A new and distinct variety of rose plant of the, compact floribunda class, substantially as herein illustrated and described as a distinct and novel rose variety due to its abundant, pale orange colored flowers, vigorous and compact growth, year round flowering under glasshouse conditions, suitability for production from softwood cuttings in pots, and durable flowers and foliage which make the variety suitable for distribution in the floral industry.

* * * * *

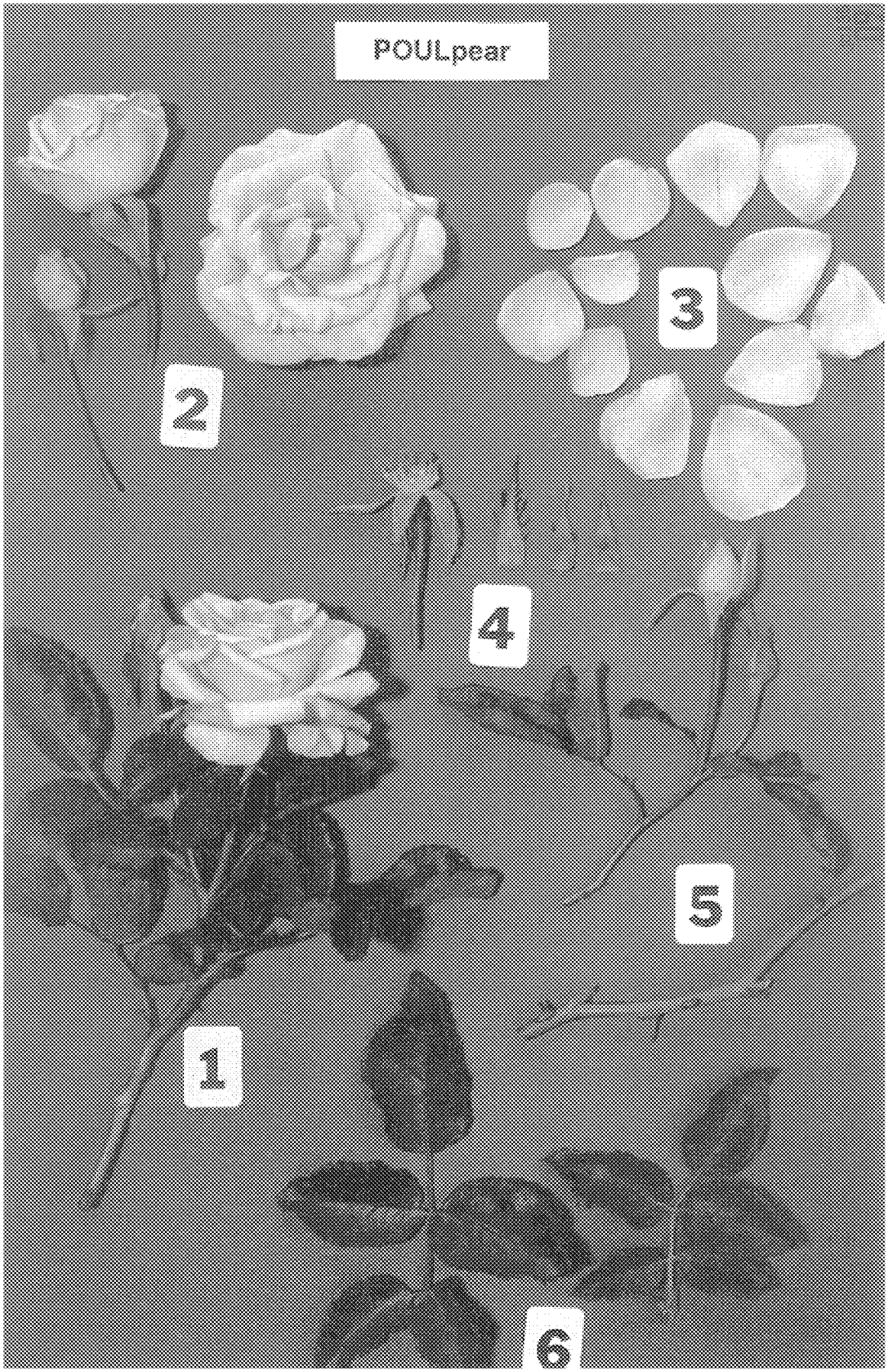
POULpear
1
2
3
4
5
6